United States Patent [19]

Hobbs et al.

[11] Patent Number: 4,835,334
[45] Date of Patent: May 30, 1989

[54] TWO-STAGE ADSORPTIVE SEPARATION PROCESS FOR PURIFYING 2,6 DIMETHYLNAPHTHALENE

[75] Inventors: Simon H. Hobbs, Chicago; Timothy J. Barder, Addison, both of Ill.

[73] Assignee: UOP, Des Plaines, Ill.

[21] Appl. No.: 174,561

[22] Filed: Mar. 29, 1988

[51] Int. Cl.$^4$ .............................................. C07C 7/12
[52] U.S. Cl. ................................ 585/831; 208/310 Z
[58] Field of Search .................... 505/831; 208/310 Z

[56] References Cited

U.S. PATENT DOCUMENTS

| | | | |
|---|---|---|---|
| 2,564,532 | 8/1951 | Hirschler | 585/831 |
| 2,967,896 | 1/1961 | Fleck et al. | 585/831 X |
| 3,133,126 | 5/1964 | Fleck et al. | 585/831 |
| 3,668,267 | 6/1972 | Hedge | 208/310 Z |
| 3,707,550 | 12/1972 | Stine et al. | 505/831 X |
| 3,772,267 | 11/1973 | Hedge | 260/674 SA |
| 3,840,610 | 10/1974 | Hedge | 585/831 |
| 3,895,080 | 7/1975 | Davis | 585/831 |
| 3,957,896 | 5/1976 | Yokoyama et al. | 585/779 |
| 4,014,949 | 3/1977 | Hedge | 208/310 Z X |

OTHER PUBLICATIONS

Japanese Public Disclosure 240632/87 dated 10/21/87 (T. Taniguchi and the other).

*Primary Examiner*—Glenn Caldarola
*Attorney, Agent, or Firm*—Thomas K. McBride; John F. Spears, Jr.; John M. Stec

[57] ABSTRACT

A two stage adsorptive separation process for recovering purified 2,6 Dimethylnaphthalene ["2,6 DMN"] from a fresh feed mixture comprising 2,6 DMN and at least one isomer thereof, which process comprises a first stage, employing a first stage adsorbent and desorbent material and operating at 2,6 DMN rejective conditions, with at least a portion of the raffinate product of such stage being fed to a second stage, employing a second stage adsorbent and desorbent material and operating at 2,6 DMN extractive conditions, thereby producing a second stage extract product containing purified 2,6 DMN. The adsorbent(s) and desorbent material(s) used in the process will depend upon the embodiment of the process employed. The most preferred embodiment of the subject invention concerns the use of a distinct adsorbent in each stage and a desorbent material common to both stages.

15 Claims, 1 Drawing Sheet

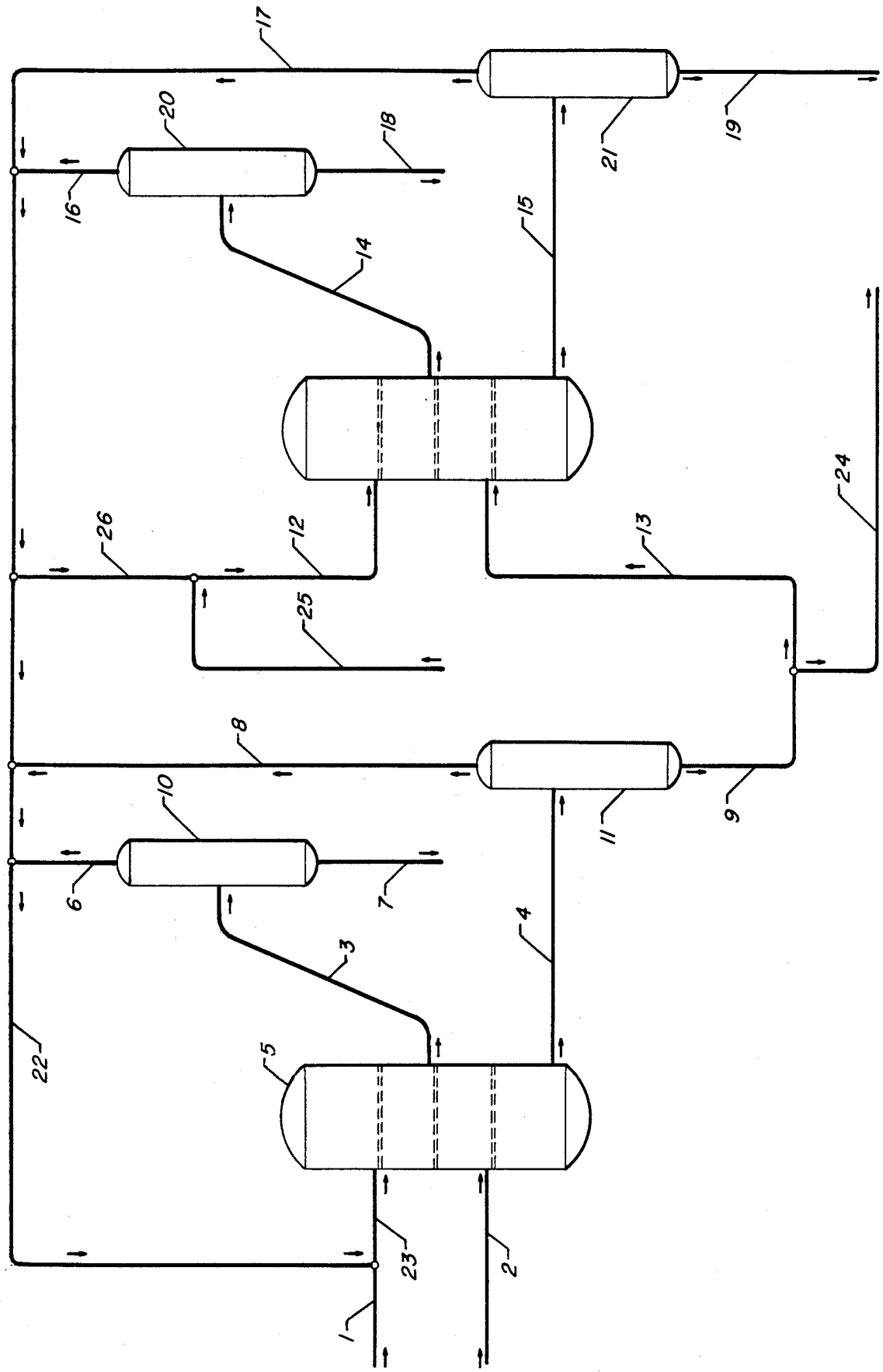

TWO-STAGE ADSORPTIVE SEPARATION PROCESS FOR PURIFYING 2,6 DIMETHYLNAPHTHALENE

BACKGROUND OF THE INVENTION

1. FIELD OF THE INVENTION

The invention relates to the separation of hydrocarbons through the use of adsorptive separation in which a feed stream containing an admixture of hydrocarbons is contacted with a solid adsorbent which selectively reatins one or more of the hydrocarbons. The invention specifically relates to the solid bed adsorptive separation of 2,6 dimethylnaphthalene ["2,6 DMN"]from a feed stream comprising a mixture of dimethylnaphthalene ["DMN"]isomers. More specifically, the invention relates to an adsorptive separation process for purifying 2,6 DMN from a feed mixture comprising DMN isomers by emplying an appropriate adsorbent/desorbent system operated in a two-stage configuration.

2. BACKGROUND INFORMATION

High purity 2,6 DMN is an important intermediate material to the production of 2,6 Naphthalenedicarboxylic acid ["2,6 NDCA"]. Moreover, polymers derived from 2,6 NDCA are known to possess properties that make them more desirable in certain applications compred to other polymers such as those derived from terephthalic acid. Such preferred polymers include those such as polyesters, polyamides, and polyaramides.

It is commercially possible to obtain 2,6 DMN from certain common industrial sources, namely, heavy catalytic reformate, fluid catalytic cracking process recycle oil or coal tar. Alternatively, it is possible to synthesize an isomeric mixture of DMN's.

Regardless of the source of the 2,6 DMN, such material is invariably found in conjunction with an isomeric mixture of dimethylnaphthalenes and other impurities which make the purification of 2,6 DMN a less than simple matter. Particularly difficult is the separation of the mixture of the 2,6 DMN and 2,7 DMN isomers which, during the purification operation, form a binary eutectic mixture of approximately 42% 2,6 DMN and 58% 2,7 DMN. This eutectic cannot be broken by distillation or solvent crystallization.

Current methods of obtaining high purity 2,6 DMN involve the use of sequential unit operations such as adsorptive separation followed by crystallization and/or complexing reactions to achieve a high purity 2,6 DMN product.

For example, Hedge teaches, in U.S. Pat. No. 3,668,267, that an adsorptive separation process, using a sodium-exchanged, type Y zeolite adsorbent in conjunction with a subsequent crystallization step, can be used to obtain acceptable pure 2,6 DMN. In such case, the adsorptive step selectively rejected 2,6 DMN to a raffinate stream which stream was, in turn, used as the feed to the crystallization stage. Hedge also disclosed the capability of a type L-zeolite to selectively adsorb the 2,6 DMN isomer from a DMN feed mixture, however, the aforesaid two-stage process (i.e., adsorptive separation followed by crystallization) was disclosed to produce a 2,6 DMN product of superior quality.

Subsequently, Hedge, in U.S. Pat. No. 3,772,399 teaches a method of separating 2,6 DMN from a mixture containing 2,6 DMN and 1,5 DMN, using a partially dehydrated type L zeolite adsorbent.

Japanese Disclosure No. 240632/87 is believed pertinent to the extent that therein is taught the tendency of 2,6 DMN to be more strongly adsorbed onto a potassium-exchanged type X zeolite adsorbent, relative to the 1,4 DMN isomer. To the contrary, we have discovered that such adsorbent, when used with either a toluene or monochlorobenzene desorbent material, always exhibits a tendency to reject the 2,6 DMN isomer relative to the other DMN isomers.

It is believed pertinent that the prior art adsorption processes have been largely concerned with other than 2,6 DMN adsorptive operations and that the final purification of 2,6 DMN is accomplished in the prior art by non-adsorptive means after the adsorptive removal of the other eutectic constituent, e.g. 2,7 DMN.

SUMMARY OF THE INVENTION

We have discovered that it is possible to effect the purification of 2,6 DMN from a mixture of DMN isomers and other contaminants in a wholly adsorptive two-stage separation process using, in one embodiment, an adsorbent/desorbent combination common to both stages, wherein, during the first stage, the 2,6 DMN is rejected to a raffinate stream and the remaining DMN isomers are adsorbed, which operation is followed by a second stage operation wherein the 2,6 DMN is adsorbed from the now non-2,6 DMN depleted material. In other embodiments, a two stage, two adsorbent system with a common desorbent is employed. If extraordinary 2,6 DMN product purity is desired, it will be recognized that such two stage process may be augmented by the addition of a final crystallization stage or other conventional means of the prior art.

Also disclosed herein is the ability to employ the first stage of our process in conjunction with and preceded and/or followed by fractionation stage(s) of the prior art so as to obtain an enhanced purity 2,6 DMN product, although such operation is not the preferred embodiment of our invention.

In brief summary, the invention is, a two-stage adsorptive separation process for obtaining purified 2,6 DMN from a feed mixture comprising 2,6 DMN and at least one isomer thereof, such process comprising a first stage, containing a first stage adsorbent and operating at 2,6 DMN rejective conditions, with at least a portion of the raffinate product of such stage being fed to a second stage, containing a second stage adsorbent and operating at 2,6 DMN extractive conditions, thereby producing a second stage extract product containing purified 2,6 DMN.

In the process of our invention, the most preferred embodiment concerns the use of a distinct adsorbent in each stage and a desorbent material common to both stages.

In one embodiment, the process is a two stage adsorptive separation process for recovering purified "2,6 DMN" from a fresh feed mixture comprising 2,6 DMN and at least one isomer thereof, which process comprises:

(a) introducing the fresh feed mixture, as the first stage feed material to the process; contacting the first stage feed material, at 2,6 DMN rejective conditions, with a first stage adsorbent, thereby preferentially rejecting at least a portion of the 2,6 DMN contained in the first stage feed material to a first stage raffinate stream and adsorbing the remainder of the first stage feed material; removing the adsorbed portion of the first stage feed material from the first stage adsorbent by desorption, with a first stage desorbent material, at desorptive conditions to produce a first stage extract stream; and (b) introducing at least a portion of the first stage raffinate material, as the second stage feed material to the process; contacting the second stage feed material with a second stage adsorbent, at 2,6 DMN adsorptive conditions, thereby preferentially adsorbing at least a portion of the 2,6 DMN contained in the second stage feed material and rejecting the remainder of the second stage feed material to a second stage raffinate stream; removing the 2,6 DMN from the second stage adsorbent, by desorption, with a second stage desorbent material, at desorptive conditions, thereby producing a second stage extract product stream containing purified 2,6 DMN.

Other embodiments of our invention encompass details about feed miuxtures, adsorbents, adesorbent materials and operating conditions, all of which are hereinafter disclosed in the following discussion of each of the facets of the present invention.

DISCUSSION OF THE INVENTION

Adsorptive separation processes may be performed using a variety of operating techniques. For instance, the adsorbent may be retained as a fixed bed or transported through the adsorption zone as a moving bed. In addition, techniques may be employed to simulate the movement of the adsorbent bed. The adsorptive separation zone can therefore comprise a simple swing-bed system with one or more beds of adsorbent being used to collect the desired chemical compound(s) while previously used beds are being regenerated by the use of a desorbent and possibly by a simultaneous temperature increase, pressure decrease, or a combination of two or more of these commonly used regeneration techniques. A further possible variation in the operation of the adsorptive separation zone results from the possibility of operating the adsorbent beds under either vapor phase or liquid phase conditions. The use of liquid phase methods is preferred. Certain benefits are obtained by using a simulated moving bed of adsorbent. These benefits include the continuous production of a high purity product stream while avoiding attrition of the adsorbent. Preferably, the countercurrent flow of the bed of solid adsorbent and the various entering liquid streams, such as the feed and desorbent streams, is simulated.

Two separate actions are involved in this simulation. The first of these is the maintenance of a net fluid flow through the fed of adsorbent in a direction opposite to the direction of simulated movement of the adsorbent. This is performed through the use of a pump operatively connected in a manner to achieve this circulation along the length of the entire bed of adsorbent. The second action involved in simulating the movement of the adsorbent is the periodic actual movement of the location of the various zones, such as the adsorption zone, along the length of the bed of adsorbent. This actual movement of the location of the various zones is performed gradually in a unidirectional pattern by periodically advancing the points at which the entering streams enter the adsorbent bed and the points at which the effluent streams are withdrawn from the adsorbent bed. It is only the locations of the zones as defined by the respective feed and withdrawal points along the bed of adsorbent which are changed. The adsorbent bed itself is fixed and does not move.

The bed of adsorbent may be contained in one or more separate interconnected vessels. At a large number of points along the length of the bed of adsorbent, typically 8–20, the appropriate openings and conduits are provided to allow the addition or withdrawal of liquid. At each of these points, there is preferably provided a constriction of the cross-section of the bed of adsorbent by a liquid distributor-collector. These may be similar to the apparatus described in U.S. Pat. Nos. 3,208,833; 3,214,247; and 3,523,762. These distributor-collectors serve to aid in the establishment and maintenance of plug flow of the fluids along the length of the bed of adsorbent. The two pints at which any one stream enters and the corresponding effluent stream leaves the bed of adsorbent are separated from each other by at least two or more potential fluid feed or withdrawal points which are not being used. For instance, the feed stream may enter the adsorption zone at one point and flow past nine potential withdrawal points and through nine distributor-collectors before reaching the point at which it is withdrawn from the adsorbent bed as the raffinate stream.

The gradual and incremental movement of the adsorption zone is achieved by periodically advancing the actual points of liquid addition or withdrawal to the next available potential point. That is, in each advance of the adsorption zone, the boundaries marking the beginning and the end of each zone will move by the relatively uniform distance between two adjacent potential points of liquid addition or withdrawal. The majority of the zone is unaffected and remains intact since the zone extends past several of these fluid transfer points.

The switching of the fluid flows at these many different locations may be achieved by a multiple-valve manifold or by the use of a multiple-port rotary valve. A central digital controller is preferably used to regulate the operation of the rotary valve or manifold.

It is important to note that an adsorptive separation process unit, as any process operation "unit", may be serially connected, in stages, to other adsorptive separation process unit(s) to effect a desired overall operational result. Generally this is not necessary, insofar as an adsorbent and desorbent system employed in the individual unit operation is normally selected so as to be adequate to effect the desired separation in a single stage operation. However, to the extent that such single stage adsorptive separation is not capable of achieving the desired product, two or more such stages may be linked serially to effect such result.

It will be clear to one ordinarily skilled in the art that such staging may be accomplished in the same apparatus if the stages are performed, with intermediate product storage, in an appropriate time sequence that is, in a "blocked-out" operating mode. Of course, such blocked-out operation in an adsorptive separation process is only likely to be economically fesible on a commercial basis, given the complexity of adsorbent loading and unloading, if the same adsorbent is used in both stages. Moreover, the similarity or incompatibility of physical and/or chemical properties of the desorbent(s) required in each stage may determine the feasibility of utilizing a blocked-out, staged operation.

Furthermore, ordinarily, in a staged process, each stage accomplishes the same purpose and in the same manner as the stage(s) which precede it, however, the product of such downstream stage(s) is (are) improved relative to the product of the upstream stage(s) because of the enhanced quality of the material fed to such downstream stage(s) relative to the material fed to the upstream stage(s). Thus, ordinarily, each stage is an operational replicate of each other stage. However, such need not necessarily be the case. Note that is is possible to utilize the same apparatus for two distinct unit operations depending upon the operating technique employed in such stage(s) at the time in question. For example, a distillation column may be used to separate various mixtures depending, among other things, upon the amount of energy input into the reboiler of the column and the flow rates into, within and out of the column. Correspondingly, in one embodiment of our invention we alter the operation of a single adsorbent-/desorbent apparatus by appropriate adjustment of the external flow rates of the stage. That is, specifically, in one embodiment of our invention, by merely varying one or more of the unit operation's external flow rates, we can selectively direct the desired compoennt (in this case 2,6 DMN) of the feed stream to either the extract stream (i.e., 2,6 DMN extractive conditions) or raffinate stream (i.e., 2,6 DMN rejective conditions) of such such stage, without changing the type of adsorbent or desorbent in such apparatus. Such a purely operating variable change allows for the employment of an efficient blocked-out operation in a single apparatus. Furthermore, we have discovered the appropriate adsorbent-desorbent combination which allows for this operating technique to be employed for purifying 2,6 DMN. Specifically, the use of a potassium-exchanged type X zeolite and a desorbent comprising toluene has been shown to function adequately.

In a preferred embodiment of our invention we have discovered that the two-stage process of our invention is more efficiently practiced using two separate unit operations apparatus. Each such stage utilizes an appropriate, but distinct, adsorbent material and a common desorbent material. Although such a dual adsorbent system could be run in a single apparatus, in a blocked-out manner, as aforesaid, it would usually be impractical to intermediately store interstage product(s) and tolerate the requisite process downtime between alternating stage operations.

In the following discussion of the particular terms applicable to the practice of our invention, it is important to realize that, unless otherwise specified, each term will have applicability to each of the two stages of the process.

As used herein, the term "feed stream" of a stage in question, is intended to indicate a stream in the process which comprises the feed material to such stage and which is charged to the bed of adsorbent associated with such stage for the purpose of recovering the desired component(s) of the feed material. The feed stream to such stage will comprise one or more extract components and one or more raffinate components. An "extract component" is a chemical compound which is preferentially adsorbed by the adsorbent associated with such stage as compared to a "raffinate component". Normally the term "extract component" is synonymous with the desired product of the process. However, since our process comprises a two-stage rejective and adsorptive operation with respect to 2,6 DMN, this is not necessarily so. For instance, in the preferred embodiment of the subject process, during the second stage, that is during the operation of the process at 2,6 DMN extractive conditions, 2,6 DMN is selectively adsorbed compared to other material present in the second stage feed material and is the extract component which is recovered as the second stage product.

Note however that the 2,6 DMN is rejected during the first stage to the raffinate stream and thus, although 2,6 DMN is the desired product of the overall process of a particular stage, is not the extract component of the first stage of the process. The other chemical compounds which were contained in the feed stream, which in the first stage are mainly other than 2,7 DMN and which in the second stage of the preferred embodiment are mainly other DMN isomers, become the raffinate components of the stage in question. In any event, in the case at hand, the 2,6 DMN-rich extract of the second stage of the process would be considered the final product of our overall process.

The term "extract stream" refers to a stream which contains extract components originally contained in the feed stream to the stage in question and which have been desorbed from the bed of adsorbent by the desorbent stream. the composition of the extract stream as it leaves the bed of adsorbent will normally vary with time and can range froma bout 100 mole percent extract components to about 100 mole percent desorbent components. The term "raffinate stream" is intended to indicate a stream originating at the bed of adsorbent associated with the stage in question and which contains the majority of the raffinate components of the feed stream to the stage in question. The raffinate stream is basically the unadsorbed (i.e., rejected) components of the feed stream plus desorbent components which are picked up during passage through the adsorption zone. Both the extract stream and the raffinate stream are normally passed into a backmixed accumulation zone before being passed into the respective fractionation columns for depletion and recovery of the desorbent materiaql associated therewith.

As used herein, the term "desorbent" is intended to indicate a chemical compound capable of desorbing the extract component from the bed of adsorbent. A "desorbent stream" is a process stream in which the desorbent is carried to the bed of adsorbent. The desorbent is preferably a hydrocarbon which may be separated from the extract and the raffinate components quite readily by fractional distillation. The desorbent should therefore have a different boiling point, preferably lower than both the extract and raffinate components. In the preferred embodiment of our invention, the desorbent stream is preferably rich in toluene or chlorobenzene and most preferably chlorobenzene.

Configurations for the adsorptive separation zone and the preferred simulated moving bed technique is described in some detail in U.S. Pat. Nos. 3,392,113; 3,455,815; and 4,006,197 and 2,985,589 which are incorporated herein by reference. These references describe operating conditions and methods and adsorbents for use in the separation of hydrocarbons. Further information on adsorptive techniques and the preferred operating methods may be obtained by reference to U.S. Pat. Nos. 3,617,504; 4,133,842; and 4,434,051, which are incorporated herein by reference. Information on a suitable rotary valve design is avilable in U.S. Pat. No. 3,040,777.

Another embodiment of a simulated moving bed flow system suitable for use in the process of the present invention is the cocurrent high efficiency simulated moving bed process disclosed in U.S. Pat. No. 4,402,832 to Gerhold, incorporated by reference herein it its entirety.

The preferred operating conditions for the adsorbent containing chambers used in the separation stage include a temperature of from 20 to about 250 degrees Celsius and a pressur of from atmospheric to about 1500 kPa g. The pressure is normally set as being sufficient to maintain liquid phase conditions within all points of the adsorptive separation process. A temperature of from 150 to 200 degrees Celsius and a pressure between 800 and 1200 kPa g are highly preferred. The adsorbents which are most preferred for the separation of 2,6 DMN from a feed mixture comprising 2,6 DMN and its isomers, comprise a potassium exchanged, type X zeolite adsorbent and a carbon adsorbent, having a pore opening of a size sufficient to allow the 2,6 DMN and desorbent molecules access thereto without undue interference therewith, such carbon being exemplified by the type commercially available as "Type OL-Carbon" from the Calgon Corporation.

BRIEF DESCRIPTION OF THE FIGURE

The accompanying figure is a schematic representation of the process flow of a simulated moving bed embodiment of this invention, which shows the interrelation of the two stages of the unit operations comprising out invention.

DETAILED DESCRIPTION OF THE FIGURE

The accompanying figure, as aforesaid, is a schematic representation of our process. Line 1 is the make-up desorbent to the first stage of the process; line 23 is the desorbent input to the first stage; line 2 is the fresh feed to the first stage; line 3 is the extract product of the first stage; line 4 is the raffinate product of the first stage; vessel 5 is the first stage adsorbent chamber (vessel); line 6 and line 7 are, respectively, the desorbent product and first stage extract product from vessel 10, the extract/desorbent recovery means of the first stage; line 8 and line 9 are, respectively, the desorbent product and first stage raffinate product from vessel 11, the raffinate/desorbent recovery means of the first stage; line 25 is the make-up desorbent input to stage two; line 26 is a portion of the recovered desorbent from the various desorbent recovery means of the process and is the desorbent input to the second stage of the process; line 12 is the desorbent input to stage two; line 24 is the first stage raffinate material withdrawal; line 13 is at least a portion of the first stage raffinate material of line 9 which portion of such material comprises the feed to the second stage of the process. Line 14 is the extract product of the second stage of the process; line 15 is the raffinate product of the second stage; line 16 and line 17 are, respectively, the desorbent recovery streams of the second stage extract and raffinate recovery means, vessels 20 and 21; line 18 is the second stage extract product and line 19 is the second stage raffinate product; line 22 is the composite stream of the desorbent revoery means' desorbent streams which is shown to be routed back to provide desorbent for the continuous operation of the first stage of the process.

PREFACE TO THE EXAMPLES

The following non-limiting examples are presented to illustrate the process of the present invention and are not intended to unduly restrict the scope of the claims attached hereto. Each of the three following examples demonstrates the utility of a particular embodiment of the claimed invention, with the embodiment demonstrated by Example III being the most preferred. Insofar as no single apparatus was available to conduct the work comprising the basis of the examples, it was necessary to simulate the practice of the two-stage process embodiments by the alternative practice of each stage of the embodiment in question so as to emulate the practice of a contiguous two-stage process. It will be noted from the data that such two-stage synthesis results in a discontinuity in the interstage process stream compositions. Specifically, the first stage raffinate stream composition is not necessarily equivalent to the second stage feed stream composition. In fact the data shown in the examples for each process stream is actual plant data and the aforesaid discontinuity is neither a necessary or desirable element of our process but merely shows the flexibility of our process in accommodating variations in process stream compositions.

EXAMPLE I

A simulated countercurrent moving bed plant of the type described above and corresponding to the schematic flowscheme described in FIG. I was prepared for operation at the following conditions:

| Adsorbent Type: | Potassium-exchanged X zeolite | |
|---|---|---|
| Adsorbent Volume: | 515 cc | |
| Feed Rate: | 28.0 cc/hr | |
| Desorbent Rate: | 500 cc/hr | |
| Rotary valve cycle time: | 1.0 hour | |
| Operating Temperature: | 200° C. | |
| Desorbent: | 100% Toluene | |
| Feed Composition: | Component | Wt. % |
| | 2,6 DMN | 12.5 |
| | Other DMN | 57.3 |
| | Others | 30.2 |
| | Total | 100.0 |

The plant was operated at the above conditions in the 2,6 DMN rejective mode, that is in such manner so that the 2,6 DMN preferentially is directed to the raffinate stream. In so doing, during one particular test run of the plant, 85 cc/hr of raffinate product was obtained:

| First Stage Raffinate | Component | Wt. % |
|---|---|---|
| Product Composition: | 2,6 DMN | 68.2 |
| (on a desorbent-free | Other DMN | 2.8 |
| basis) | Others | 29.0 |
| | Total | 100.0 |

This first stage raffinate stream was then directed to storage in preparation for stage two of our process.

For stage two, the same simulated moving bed plant which was used for stage one was prepared for operation at the following conditions:

| Adsorbent Type: | same as stage No. 1 |
|---|---|
| Adsorbent Volume: | same as stage No. 1 |
| Feed Rate: | 27.5 cc/hr |
| Desorbent Rate: | 550 cc/hr |
| Rotary valve step time: | 1.0 hour |
| Operating Temperature: | 175° C. |
| Desorbent: | 100% Toluene |

During the second stage of our process, the plant was operated at the above conditions in the extractive mode, that is in such manner so that the 2,6 DMN preferentially is directed to the extract stream. The feed to the pilot plant during this second stage of our process was a desorbent-free portion of the composite of first stage raffinate product obtained over a period of time and numerous test runs.

| Second Stage | Component | Wt. % |
|---|---|---|
| Feed Composition: | 2,6 DMN | 71.5 |
| (on a desorbent-free | Other DMN | 1.2 |
| basis) | Others | 27.3 |
| | Total | 100.0 |

In so doing, 265 cc/hr of extract product was obtained:

| Second Stage Extract | Component | Wt. % |
|---|---|---|
| Product Composition: | 2,6 DMN | 78.2 |
| (on a desorbent-free | Other DMN | 1.5 |
| basis) | Others | 20.3 |
| | Total | 100.0 |

Because this second stage extract product purity (that is, wt. % 2,6 DMN) obtained was lower than the commercially desirable value of 90 wt %, a further distillative fractionation was performed to remove otherwise easily fractionable impurities. The resultant product of this final finishing distillation was over 90 wt. % 2,6 DMN. The ultimate loss of 2,6 DMN during such distillation would be dependent upon the sophistication of the fractionation means employed. It should be mentioned that such final finishing distillation procedure may or may not be necessary, depending upon the extent to which impurities are present in the feed to the first stage of our process. Obviously, insofar as no change in properties of these impurities occurs in the course of our two-stage process, such material may be fractionated prior to processing in our process, rather than subsequent thereto, in accordance with the requirements of the specific commercial installation.

EXAMPLE II

A simulated countercurrent moving bed pilot plant of the type described above was prepared for operation at the conditions specified in Example I for the first stage operation, thereby producing a first stage raffinate product stream equivalent to that obtained in Example I. This product stream was then directed to storage in preparation for stage two of our process.

For stage two, a simulated moving bed pilot plant of the same type which was used for stage one was prepared for operation at the following conditions:

| Adsorbent Type: | Calgon Type OL Carbon |
|---|---|
| Adsorbent Volume: | 515 cc |
| Feed Rate: | 32.4 cc/hr |
| Desorbent Rate: | 666 cc/hr |
| Rotary valve cycle time: | 1.0 hour |
| Operating Temperature: | 200° C. |
| Desorbent: | 100% Toluene |

In so doing, 334 cc/hr of extract product was obtained:

| Second Stage Extract | Component | Wt. % |
|---|---|---|
| Product Composition: | 2,6 DMN | 94.2 |
| (on a desorbent-free | Other DMN | 1.3 |
| basis) | Others | 4.5 |

-continued

| Second Stage Extract | Component | Wt. % |
|---|---|---|
| | Total | 100.0 |

Thus, the purity of the ultimate 2,6 DMN product produced by this embodiment of our invention was commercially acceptable (i.e., $\geq$90 wt. % 2,6 DMN) without the need to perform a finishing distillation step.

EXAMPLE III

A simulated countercurrent moving bed pilot plant of the type described above was prepared for operation at the following conditions:

| Adsorbent Type: | Potassium-exchanged X zeolite | |
|---|---|---|
| Adsorbent Volume: | 515 cc | |
| Feed Rate: | 28.0 cc/hr | |
| Desorbent Rate: | 520 cc/hr | |
| Rotary valve cycle time: | 1.0 hour | |
| Operating Temperature: | 170° C. | |
| Desorbent: | 100% Monochlorobenzene | |
| Feed Composition: | Component | Wt. % |
| | 2,6 DMN | 10.5 |
| | Other DMN | 52.2 |
| | Others | 37.3 |
| | Total | 100.0 |

The plant was operated at the above conditions in the 2,6 DMN rejective mode, that is in such manner so that the 2,6 DMN was preferentially directed to the raffinate stream. In so doing 160 cc/hr of raffinate product was obtained:

| First Stage Raffinate | Component | Wt. % |
|---|---|---|
| Product Composition: | 2,6 DMN | 60.9 |
| (on a desorbent-free | Other DMN | 1.1 |
| basis) | Others | 38.0 |
| | Total | 100.0 |

This first stage raffinate product stream was then directed to storage in preparation for stage two of our process.

For stage two, a simulated moving bed pilot plant of the same type used for stage one was prepared for operation at the following conditions:

| Adsorbent Type: | Calgon Type OL Carbon |
|---|---|
| Adsorbent Volume: | 515 cc |
| Feed Rate: | 20.6 cc/hr |
| Desorbent Rate: | 525 cc/hr |
| Operating Temperature: | 170° C. |
| Desorbent: | 100% Monochlorobenezene |

The feed to the pilot plant during this second stage of our process was, as aforesaid, a desorbent-free portion of the first stage raffinate product. Hence, the composition of the feed stream to stage two of our process in this example was as follows:

| Second Stage | Component | Wt. % |
|---|---|---|
| Product Composition: | 2,6 DMN | 75.4 |
| (on a desorbent-free | Other DMN | 1.1 |
| basis) | Others | 25.5 |

-continued

| Second Stage | Component | Wt. % |
|---|---|---|
| | Total | 100.0 |

The plant was operated at the above conditions in the 2,6 DMN extractive mode, that is, in such a manner so that the 2,6 DMN is preferentially directed to the extract stream. In so doing, 160 cc/hr of extract product was obtained:

| Second Stage Extract | Component | Wt. % |
|---|---|---|
| Product Composition: | 2,6 DMN | 95.8 |
| (on a desorbent-free | Other DMN | 1.3 |
| basis) | Others | 2.9 |
| | Total | 100.0 |

DISCUSSION OF THE EXAMPLES

In general, the above data does show that the present two stage invention provides a 2,6 DMN selective system with adequate selectivities for the commercial use thereof. It has been shown, specifically, that one embodiment of the present invention is capable of upgrading the 2,6 DMN purity of a feed mixture from approximately 12.5 wt % to over 78 wt %, which product, in turn, was shown to be easily fractionable by common distillation to obtain a commercially acceptable final product purity of over 90 wt %; although such adsorption/distillation process is not the preferred embodiment of our invention.

The foregoing Examples II and III also demonstrate the superiority, with respect to ultimate product purity, of the preferred and most preferred embodiments of our invention compared to that demonstrated by Example I. In Example II, the 2,6 DMN product purity was in excess of 94 wt. % and in Example III, the 2,6 DMN product purity exceeded 95 wt %. Thus, in both Examples II and III, it has been demonstrated that a commercially acceptable 2,6 DMN product may be obtained in a wholly adsorptive separation process, that is, without the requirement of the final distillation, crystallization or other non-adsorptive separation techniques of the prior art.

We claim as our invention:

1. A two-stage adsorptive separation process for obtaining purified 2,6 DMN from a feed mixture comprising 2,6 DMN and at least one isomer thereof, such process comprising a first stage, employing a first stage adsorbent comprising a potassiumexchanged X zeolite and a first stage desorbent material and operating at 2,6 DMN rejective conditions and isomer adsorption conditions to adsorb said isomer from said feed mixture to yield a 2,6 DMN containing raffinate product with at least a portion of 2,6 DMN the raffinate product of such stage being fed to a second stage, employing a second stage adsorbent comrpsing a potassium-exchanged X zeolite and a second stage desorbent material and operating at 2,6 DMN adsorptive conditions, to adsorb said 2,6 DMN.

2. The process of claim 1 wherein both stages of the process are carried out in the same apparatus, in sequence.

3. The process of claim 2 wherein the first stage desorbent material and the second stage desorbent material each comprises toluene.

4. The process of claim 3 wherein the adsorptive and desorptive conditions include a temperature within the range of from about 20° C. to about 200° C. and a pressure sufficient to maintain liquid phase.

5. The process of claim 4 wherein said process is effected with a simulated moving bed flow system.

6. The process of claim 4 wherein said process is effected with a static bed system.

7. The process of claim 5 wherein the simulated moving bed is operated in either a cocurrent or countercurrent manner.

8. A two-stage adsorptive separation process for obtaining purified 2,6 DMN from a feed mixture comprising 2,6 DMN and at least one isomer thereof, such process comprising a first stage, employing a first stage adsorbent comprising a potassiumexchanged X zeolite and a first stage desorbent material and operating at 2,6 DMN rejective conditions and isomer adsorption conditions to adsorb said isomer from said feed mixture to yield a 2,6 DMN containing raffinate product with at least a portion of the 2,6 DMN raffinate product of such stage being fed to a second stage, employing a second stage adsorbent comprising a carbon material and a second stage desorbent material and operating at 2,6 DMN adsorptive conditions to adsorb said 2,6 DMN.

9. The process of claim 8 wherein the first stage desorbent material and second stage desorbent material each comprises toluene.

10. The process of claim 8 wherein the first stage desorbent material and the second stage desorbent material each comprises chlorobenzene.

11. The process of claim 8 wherein the carbon material is a carbon material having a pore opening sufficiently large to permit the adsorption and desorption of 2,6 DMN and the desorbent material.

12. The process of claim 8 wherein the adsorptive and desorptive conditions include a temperature within the range of from about 20° C. to about 200° C. and a pressure sufficient to maintain liquid phase.

13. The process of claim 12 wherein said process is effected with a simulated moving bed flow system.

14. The process of claim 12 wherein said process is effected with a static bed system.

15. The process of claim 13 wherein the simulated moving bed is operated in either a cocurrent or countercurrent manner.

* * * * *

UNITED STATES PATENT AND TRADEMARK OFFICE
CERTIFICATE OF CORRECTION

PATENT NO. : 4,835,334
DATED : May 30, 1989
INVENTOR(S) : Hobbs et al.

It is certified that error appears in the above-identified patent and that said Letters Patent is hereby corrected as shown below:

In Claim 1, Column 11, Line 51:  Change "potassiumexchanged" to --potassium-exchanged--;

In Claim 1, Column 11, Line 55:  Change "product with" to --product, with--;

In Claim 8, Column 12, Line 26:  Change 'potassiumexchanged" to --potassium-exchanged--;

In Claim 8, Column 12, Line 30:  Change "product with" to --product, with--.

Signed and Sealed this

Tenth Day of April, 1990

Attest:

HARRY F. MANBECK, JR.

Attesting Officer

Commissioner of Patents and Trademarks